United States Patent [19]

Morrison, Jr.

[11] 4,074,718
[45] Feb. 21, 1978

[54] ELECTROSURGICAL INSTRUMENT

[75] Inventor: Charles F. Morrison, Jr., Boulder, Colo.

[73] Assignee: Valleylab, Inc., Boulder, Colo.

[21] Appl. No.: 667,849

[22] Filed: Mar. 17, 1976

[51] Int. Cl.² .................... A61B 17/40; A61N 3/06
[52] U.S. Cl. .................... 128/303.14; 128/303.17; 128/303.18; 219/145.21; 219/234; 219/146.21
[58] Field of Search .................. 128/303.17, 303.13, 128/303.14, 303.15, 303.18; 219/234, 145; 228/51-55

[56] References Cited

U.S. PATENT DOCUMENTS

| | | | |
|---|---|---|---|
| 1,814,791 | 7/1931 | Ende | 128/303.17 |
| 2,436,887 | 3/1948 | Hensley | 219/234 |
| 3,032,637 | 5/1962 | Wasserlein | 219/234 |
| 3,120,649 | 2/1964 | Kolterman | 219/234 |
| 3,685,518 | 8/1972 | Beurle et al. | 128/303.17 |
| 3,796,853 | 3/1974 | Matsuo et al. | 219/145 |
| 3,826,263 | 7/1974 | Cage et al. | 128/303.17 X |
| 3,902,494 | 9/1975 | Haberlen | 128/303.17 |
| 3,911,241 | 10/1975 | Jarrard | 128/303.17 X |
| 3,911,246 | 10/1975 | Drinkard, Jr. | 219/234 |
| 3,920,021 | 11/1975 | Hiltebrant | 128/303.17 |

OTHER PUBLICATIONS

Sugita et al., "Bipolar Coagulator with Automatic Thermocontrol", J. Neurosurg., vol. 41, Dec. 1974, pp. 777-779.

Primary Examiner—Ronald L. Frinks
Assistant Examiner—Lee S. Cohen
Attorney, Agent, or Firm—Gerald J. Ferguson, Jr.; Joseph J. Baker

[57] ABSTRACT

An electrosurgical instrument comprising a support member; at least one electrode mounted on the support, the electrode consisting essentially of a material having a figure of merit of at least 0.15 at room temperature where the figure of merit is the product of the thermal conductivity, the heat capacity and the density of the material in the metric system; and a heat sink in thermal contact with the electrode for removal of heat therefrom. A carbon coating for the electrode is also disclosed where the coating may be formed by different techniques including thermal decomposition of certain carbohydrate containing materials, the latter method providing a porous carbon coating particularly suited for expediting the starting of the instrument. Also disclosed are a number of heat sinks for effecting removal of heat from the electrode. Further disclosed is a monolithic blade made from carbon.

47 Claims, 36 Drawing Figures

ELECTROSURGICAL INSTRUMENT

CROSS-REFERENCE TO RELATED APPLICATION

This application is related to U.S. Application Ser. No. 501,224 entitled "Improved Electrosurgical Devices Having Sesquipolar Electrode Structures Incorporated Therein" and filed Aug. 28, 1974 by Charles F. Morrison, Jr. and assigned to the assignee of the present application, the above related application being incorporated herein by reference.

BACKGROUND OF THE INVENTION

This invention relates to electrosurgery and, in particular, to electrosurgical instruments and methods of making and using them.

Heretofore, the active electrodes used in electrosurgical instruments have for the most part been made of steel, brass or stainless steel. Such electrodes have certain drawbacks. Thus, living tissue tends to adhere to these electrodes when implementing a surgical procedure such as cutting, coagulation, etc. This results in the tearing away of the tissue which can cause dangerous complications in some operations. Further, these electrodes tend to foul with the burned, adhered tissue. Thus, frequent cleaning is necessary.

Another problem associated with clogging or fouling of electrodes of the above type tends to occur with bipolar or sesquipolar devices. Refer to the above mentioned, co-pending patent application for a description of sesquipolar devices. Generally, in a sesquipolar device, arcing ideally occurs only at the active electrode where both the active and return electrodes are in the surgical site. In a bipolar device, if one electrode fouls more than the other, the clogged electrode will tend to arc preferentially thereby preventing the desired bipolar mode of operation where equal flesh interaction preferably occurs at the two electrodes. If the return electrode of a sesquipolar device clogs, there will be a tendency for arcing to occur at the return electrode. This is also undesirable since in a sesquipolar device arcing should occur only at the active electrode, as stated above.

Another problem associated with the use of electrodes of the above type is the tendency of such electrodes, when operated in the coagulation mode, to effect undesired, massive cutting of the tissue. Further, so-called "stimulation" currents tend to be associated with the use of electrodes of the above type. That is, when using such electrodes there is an undesirable tendency for nerves to be stimulated by currents of certain frequencies. Also, the amount of power required to use such electrodes tends to be high.

SUMMARY OF THE INVENTION

Thus, it is a primary object of this invention to provide an improved electrosurgical instrument having electrodes which have little, if any, tendency to tear away living tissue when in use.

It is a further object of this invention to provide an instrument of the above type where there is little, if any, tendency for the electrode to clog with burned tissue.

It is a further object of this invention to provide instruments of the above type where the tendency for undesired arcing to occur in bipolar or sesquipolar devices is lessened.

It is a further object of this invention to provide instruments of the above type where the tendency for massive cutting in the coagulation mode is lessened.

It is a further object of this invention to provide an instrument of the above type where the tendency for nerves to be stimulated by currents of certain frequencies is lessened and where the amount of power required to drive the electrodes is lessened.

It is a further object of the above invention to provide instruments of the above type where starting of cutting can be expedited whenever the electrode contacts the tissue prior to electrical energization thereof.

It is a further object of this invention to provide electrosurgical instruments having means incorporated therein for removing heat from the electrode(s) in the surgical site.

These and other objects will become apparent from a reading of the specification and claims taken with the drawing.

DETAILED DESCRIPTION OF THE PREFERRED EMBODIMENTS

Figure 1:
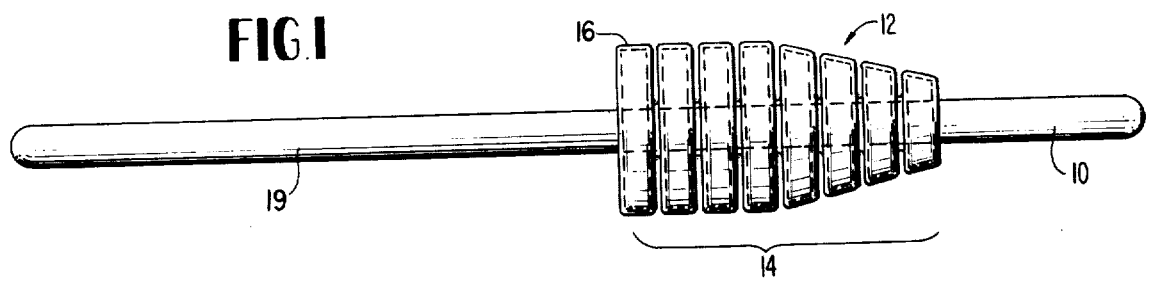
FIGS. 1 and 2 are side and end views respectively of an illustrative electrode having a heat radiator mounted thereon in accordance with one aspect of the invention.

Reference should be made to the drawing where like reference numerals refer to like elements.

Figure 2:
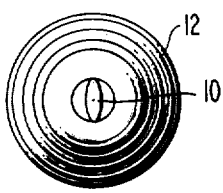

In particular, reference should be made to FIGS. 1 and 2 where there is shown an electrode blade 10 having mounted thereon a heat sink such as radiator 12, made from aluminum, for example. Radiator 12 comprises radiating elements 14 which are covered with electrically insulating material indicated at 16.

Heat radiator 12 removes heat from electrode blade 10 to maintain the temperature of the blade 10 in the range from about 0° C to about 500° C and the blade base 19 in the range from 0° C to about 100° C, or preferably from 20° C to 80° C, or more preferably from 20° C to 60° C.

In the following specification and claims, a distinction is made between electrosurgical instruments where electrical current flows through the tissue being treated from one electrode in the site to another electrode which (a) is substantially removed therefrom (monopolar mode) or (b) is also in the site or closely adjacent thereto (bipolar and sesquipolar modes). Electrical interaction between the electrode and tissue at the site may either be ohmic or by electrical discharge. The foregoing instruments will be termed "tissue current flow-type" instruments hereinafter in the specification and claims. Such electrosurgical instruments are different in kind from instruments where an electrically heated wire (hereinafter "heated-wire type" instruments) is used to seal bleeding blood vessels in hospital surgical procedures and in minor surgery performed in doctors' offices and current flows only through the electrode. This method is now being largely displaced by tissue current flow-type instruments which effect electrosurgical procedures with needle, blade and ball electrodes for example. As indicated above, these procedures involve the establishment of a radio frequency electrical current between the electrode and the tissue where current flow or electrical discharge creates the heat needed for the procedure.

In both the heated-wire type instruments and the tissue current flow-type instruments, the electrode is heated where for the latter instruments, electrical current or discharge provides heat for not only the flesh but also the electrode. The heated electrode often causes unwanted tissue destruction as the electrode is removed from the surgical site. This can result in dangerous complications in some operations. Further, it is necessary to frequently clean and electrodes due to the fouling thereof with burned tissue.

In order for an electrode to foul or stick, it is thought that all of the following conditions must be met, although there is no intent to be limited to a particular theory of operation. The electrode must contact fresh tissue when the electrode temperature is between approximately 120° C and approximately 300° C, and the electrode must maintain heat flow to the tissue equivalent to electrode temperatures above about 100° C for several tenths of a second. This is independent of electrode materials, coatings, etc. Limiting coagulation power to keep electrode temperatures below 120° C has been described in an article entitled "Bipolar Coagulator With Automatic Thermocontrol" by K. Sugita, et al., J. Neurosurgery, Vol. 41, December, 1974, pp. 777-779. However, most electrosurgical electrodes must work for both cutting and coagulation which introduces many more restraints. In order to cut, the electrode must attain a surface temperature of at least 100° C so as to maintain a steam layer between electrode and flesh. This requirement makes a massive electrode impractical for anything other than coagulation. One is thus forced to work in the cutting mode with electrode temperatures in the sticking range. As will be brought out in more detail hereinafter, high thermal conductivity materials for blade 10 and heat sinking such as that provided by radiator 12 are employed, in accordance with an important aspect of this invention, when electrosurgical cutting current is removed from blade 10, to bring the electrode to a safe temperature at sufficient rate to avoid sticking.

The above combination of high thermal conductivity materials and heat sinking also serves other important purposes. For example, when reasonably high crest factor RF waveforms are applied to conventional electrosurgical electrodes in the coagulation mode, massive cutting may occur as an interaction between waveform, power, and electrode temperature. By cooling the electrode, in accordance with this invention, it can be kept below the temperature at which cutting will occur with a given waveform and power level. Thus, the problem of massive cutting in the coagulation mode can be avoided. The critical temperature for a coagulation waveform of crest factor of about 6 and about 100 watts is approximately 200° C as will be described in more detail hereinafter. The electrode thermal properties and heat sinking system of this invention can keep the electrode below this temperature during coagulation procedures so that the troublesome massive cutting will not occur. As indicated above, the system need not keep the electrode at such a low temperature during cutting procedures. It is desirable, however, that the temperature be quickly reduced at the termination of cutting, not only to prevent fouling of the electrode, but to avoid subsequent interaction with coagulation, if the coagulation mode is switched to immediately after cutting. In summary, the same system that prevents fouling of the electrodes prevents cutting in the coagulation mode.

An electrode which conducts a sufficient amount of electrical current to ensure the formation of an electrical discharge (assuming desiccation is not being effected) is required. Also preferably required is a heat sink which removes enough heat to maintain the temperature of the electrode in the above mentioned temperature range of 0° C to about 500° C depending on whether the instrument is in the cutting or coagulation mode. The requisite current to ensure the formation of an electrical discharge varies with many factors such as electrode length, cross section and electrical conductivity together with the magnitude and wave shape of the voltage applied thereto. Typically, the current should be 0.5 - 1.0 amps.

In order to maintain the electrode at the above mentioned temperature range, up to about 6 calories of heat must be removed from it per second. Factors affecting the rate of heat removal are electrode length, cross section, thermal conductivity and sink temperature. It is not possible even with good heat dissipating means to remove heat at the required rate when a blade is constructed of a low thermal conductivity material.

Thus, blade 10 is preferably made of a high thermal conductivity material, the conductivity being at least 0.3 (Cal/sec/cm$^2$/C°-cm) and preferably at least 0.5 (Cal/sec/cm$^2$/C°-cm) although other factors affecting the electrode material will be discussed in more detail below. Thus graphite having a thermal conductivity of 0.5 is a good material for the blade, other properties permitting, while copper and silver having thermal conductivities of of 1.0 are excellent. In addition to the thermal conductivity of the electrode, additional factors relating to the electrode material are also relevant. These factors are the volume heat capacity and density of the material. Because higher thermal conductivity can compensate for lower volume heat capacity, a figure of merit (FM) for various electrode materials is employed in accordance with an important aspect of the invention. This figure of merit is equal to the product of the thermal conductitivy, the heat capacity and the density where the values are given in the metric system. The following table provides values for both good and bad electrode materials.

TABLE

| Rank | FM | Thermal Cond. | Heat Capacity | Density |
|---|---|---|---|---|
| 1 | .79 Copper | 1.0 | .09 | 8.8 |
| 2 | .53 Silver | 1.0 | .05 | 10.6 |
| 3 | .43 Gold | .70 | .03 | 19.3 |
| 4 | .41 Beryllia | .48 | .30 | 2.85 |

TABLE-continued

| Rank | FM | Thermal Cond. | Heat Capacity | Density |
|---|---|---|---|---|
| 5 | .34 Aluminum | .55 | .23 | 2.7 |
| 6 | .34 Carbon | .5 | .3 | 2.25 |
| 7 | .27 Tungsten | .48 | .03 | 19. |
| 8 | .21 Molybdenum | .35 | .06 | 10.2 |
| 9 | .13 Steel | .11 | .15 | 7.7 |
| 10 | .13 Nickel | .14 | .11 | 8.8 |
| 11 | .06 Constantan 60%Cu 40%Ni | .07 | .10 | 8.9 |
| 12 | .04 Stainless | .04 | .12 | 8.03 |
| 13 | .04 Alumina | .05 | .21 | 3.98 |

FM values are based upon metric data. Electrode materials with FM values of at least about 0.15 and preferably about 0.3 are recommended for all of the electrode embodiments described in this specification. Alloys do not rate very well relative to their components. The above values apply near room temperature. Some of them will differ by about 10% at the electrode operating temperature.

Various means for removing the heat, such as radiator 12 of FIGS. 1 and 2, will now be described. The radiating elements 14 are made from a high thermal conductivity material and, if electrically conductive, are coated with electrical insulation 16 to prevent electrical burn of either the patient or medical personnel as a result of accidental touching thereof. The radiating elements are typically, although not necessarily, circular in shape and mounted on blade 10 as indicated in FIG. 2 whereby they present a large surface area for radiating the heat at the desired rate of heat removal. The number of radiating elements 14 in radiator 12 can, of course, be so selected as to effect the desired rate of heat removal by properly choosing the total surface area and thermal conductivity thereof. These factors also are to be considered in preventing the temperature thereof from becoming so high as to cause a thermal burn. The blade 10 includes an electrically conductive base or shaft 19 which is preferably integral therewith and which permits electrical connection to an electrosurgical generator (not shown) by means of appropriate connections within the handle (not shown) into which shaft 19 may be inserted.

Figure 4:
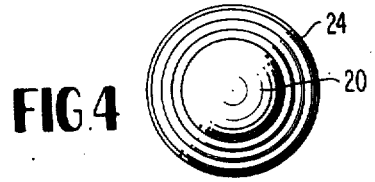
FIGS. 3 and 4 are side and end views respectively of an illustrative coagulation ball electrode having a heat radiator mounted thereon in accordance with another aspect of the invention.
Figure 3:
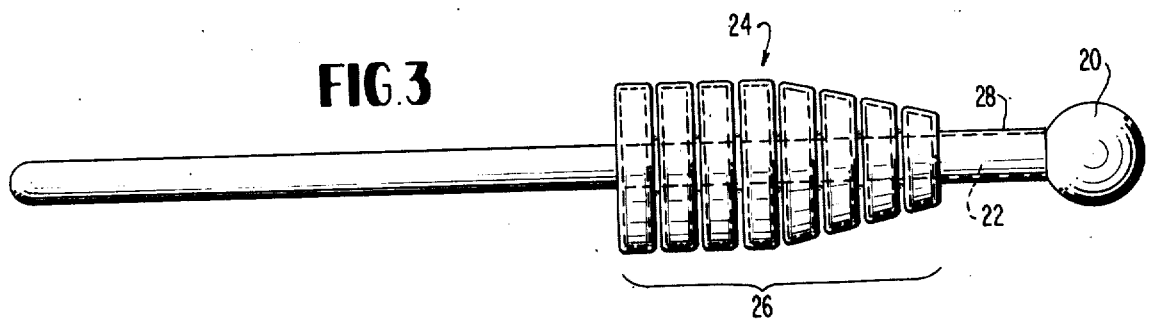

Reference should now be made to FIGS. 3 and 4 which disclose a ball electrode 20 connected to a shaft 22 (both of which preferably have high thermal and electrical conductivity) together with a radiator 24 of the type shown in FIGS. 1 and 2 where radiator 24 generally comprises a plurality of radiating elements indicated at 26. Shaft 22 should be covered with electrical insulating material 28 and so should radiator 24 if it is electrically conductive. Shaft 22 extends into a handle to facilitate electrical connection to the generator.

Figure 5:
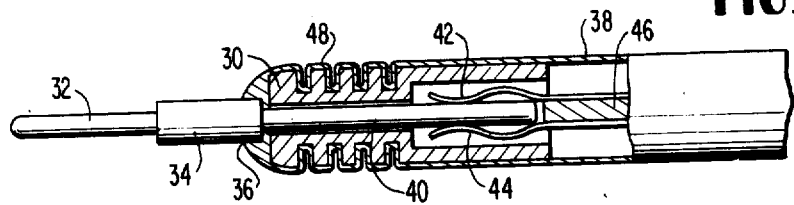
FIG. 5 is a partial cross-sectional side view of an illustrative electrosurgical instrument having a heat radiator disposed in the nose of the handle thereof in accordance with another aspect of the invention.
Figure 6:
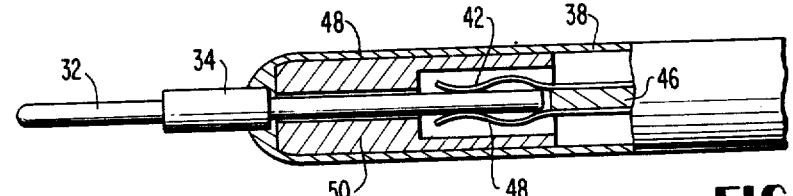
FIG. 6 is a partial cross-sectional side view of an illustrative electrosurgical instrument having a change-of-state heat sink disposed in the nose of the handle thereof in accordance with another aspect of the invention.

Reference should now be made to FIGS. 5 and 6 which disclose the incorporation of heat sinks in the nose of the handle of an electrosurgical instrument. Thus, in FIG. 5 there is disclosed a radiator-type heat sink generally indicated at 30 corresponding to the radiator type heat sinks of FIGS. 1 - 4. The blade 32 has an insulating sleeve 34 mounted thereon. Sleeve 34 is positioned within a cavity 36 in the forward portion of handle 38. A shaft 40, which is preferably an extension of electrode 32, extends into the handle. Contacts 42 and 44 engage shaft 40 and are connected to a wire 46 which extends through the handle and out the rear thereof to the "active" output terminal of the electrosurgical generator (not shown).

As can be appreciated, radiator 30 is so formed in the nose of handle 38 as to provide a large surface area for radiating heat from electrode 32. The radiator is in contact with and mounted on shaft 40 and is preferably made of a high thermal conductivity material. If the radiator material is also electrically conductive, it should be provided with an insulating coating as indicated at 48 to prevent electrical burn.

Referring to FIG. 6, a change-of-state heat sink 50 is mounted in the nose of handle 38. Preferably the material comprising the heat sink is a solid where the heat required to change the phase of the material from solid to liquid is sufficient to maintain the electrode at its desired temperature range. Radiation and convection from this sink remove heat such that the sink material eventually re-solidifies. After autoclaving or extensive use, the heat sink material can be resolidified by the above mechanism, or by placing the electrode against a cool surface or into a cool liquid.

Figure 8:
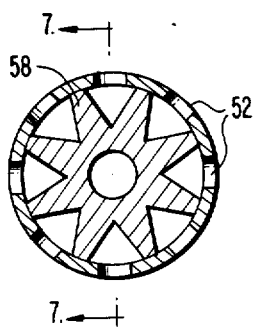
FIG. 8 is a cross-section along the line 8—8 of FIG. 7.
Figure 7:
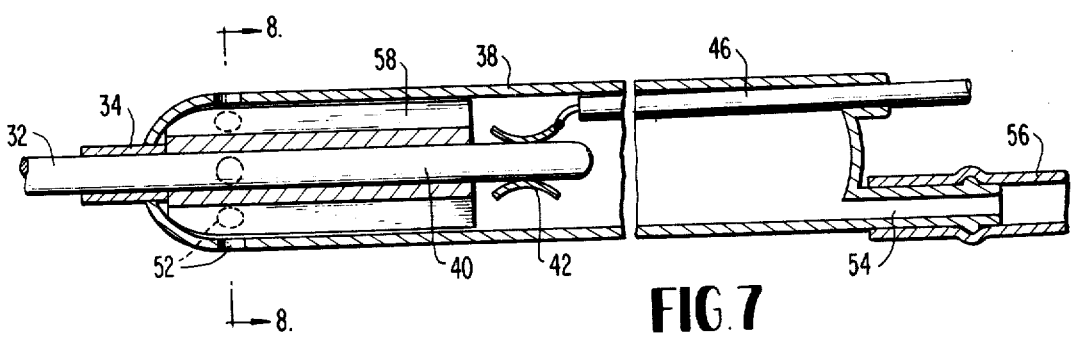
FIG. 7 is a cross-sectional view taken along the line 7—7 of FIG. 8 illustrating an electrosurgical instrument having a heat exchanger disposed in the nose of the handle thereof in accordance with another aspect of the invention.

Reference should now be made to FIGS. 7 and 8 which disclose a heat exchanger 58 where the heat of the electrode is removed by the passage of relatively cool air by the electrode. Thus, there is provided a plurality of air flow openings generally indicated at 52 about the periphery of the nose of handle 38. Outlet 54 is provided at the rear of the handle and connected via a tube 56 to a vacuum source (not shown). As can be seen in FIG. 8, a star shaped heat exchanger 58 of preferably high thermal conductivity is disposed within the nose of handle 38 and mounted on shaft 40. Each point of the star is disposed between adjacent openings 52. Thus, air is continuously drawn through holes 52 and the channels formed between the points of the star to cool electrode 32. It should be noted that the heat exchanger of FIGS. 7 and 8 can readily be used with electrode mounted, heat sink arrangements such as those shown in FIGS. 1 – 4.

Figure 9:
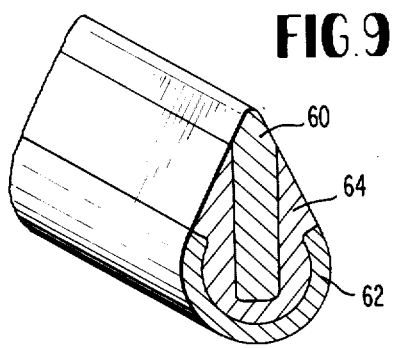
FIG. 9 is an exploded, perspective view of an illustrative sesquipolar electrode in accordance with another aspect of the invention.

In applying the foregoing heat removal principles to sesquipolar or bipolar devices, the principles remain the same. If the heat sink is electrically conductive, there must be one sink for each of the electrodes or insulation so provided that the sinks are insulated from one another as will be described hereinafter. Referring to FIG. 9, there is shown a sesquipolar instrument where the active electrode 60 and the return electrode 62 are each made of high thermal conductivity materials and have sufficient cross-section to facilitate the removal of heat therefrom to sinks (not shown) for each of the electrodes. Electrodes 60 and 62 are separated by electrically insulating support member 64.

Figure 10:
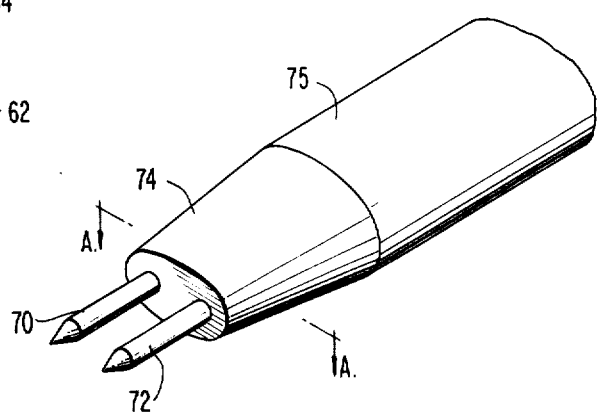
FIG. 10 is a perspective view of an illustrative bipolar needle electrode in accordance with another aspect of the invention.
Figure 11:
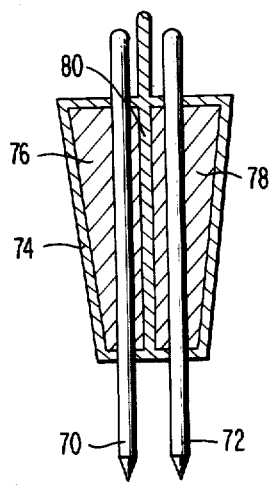
FIG. 11 is a cross-sectional view taken along line A—A of FIG. 10 illustrating two electrically conductive heat sinks in accordance with another aspect of the invention.
Figure 12:
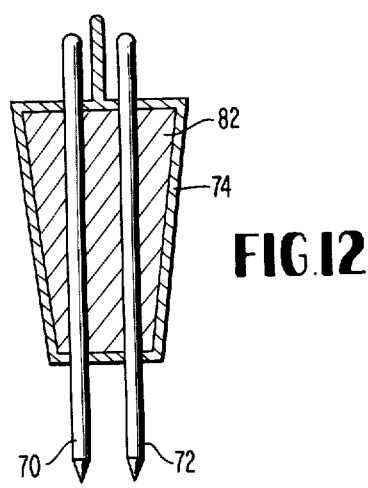
FIG. 12 is a cross-sectional view taken along the line A—A of FIG. 10 illustrating an electrically non-conductive heat sink in accordance with another aspect of the invention.

Referring to FIG. 10 there is shown a bipolar needle electrode instrument comprising needles 70 and 72 mounted within holder 74 which, in turn, is connected to a handle 75 or the like. The diameter of each needle 70 and 72 should be 0.03 inches or greater and the angle subtended by the points thereof should be 30° or more. Thus, copper or silver needles about one-half inch long should have a minimum diameter of about 0.03 inches while needles of these materials about three-quarters of an inch long should have a minimum diameter of about 0.05 inches. Further, tungsten needles about one-half inch long should have a minimum diameter of about 0.05 inches. FIGS. 11 and 12 are sections along the line A—A of FIG. 10 where in FIG. 11, an electrically conductive heat sink 76 is employed for needle electrode 70 and an electrically conductive heat sink 78 is employed for needle electrode 72. Since the heat sinks 76 and 78 are electrically conductive, an electrically insulating member 80 is disposed between the heat sinks to prevent short circuiting of the needle electrodes 70 and 72. In FIG. 12, heat sink 82 is not electrically conductive and thus no further insulation is required to electrically insulate needle electrodes 70 and 72.

Figure 13:
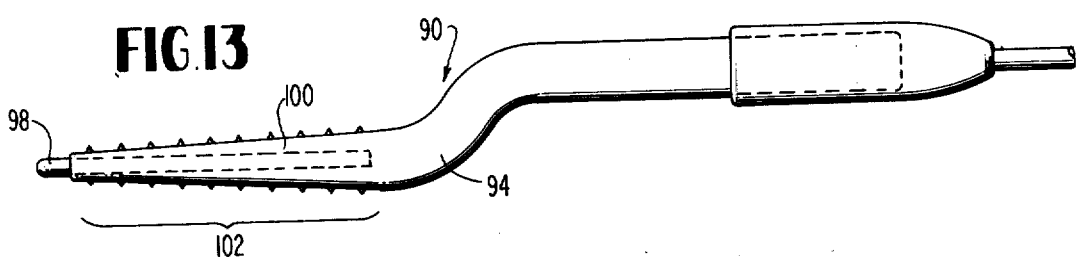
FIGS. 13 and 14 are side and plan views respectively of an illustrative forceps electrode having heat radiators disposed along the tines thereof in accordance with another aspect of the invention.
Figure 14:
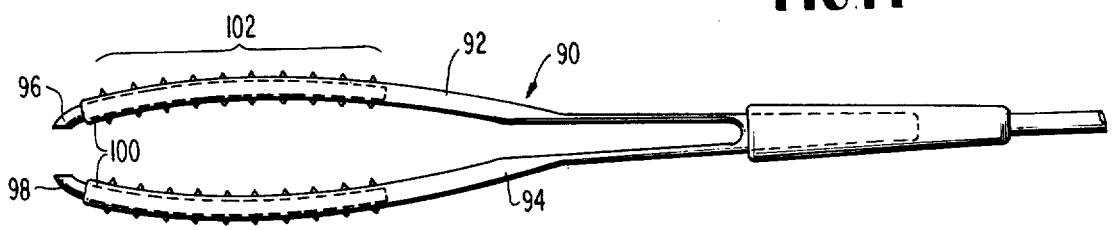

Reference should now be made to FIGS. 13 and 14 which illustrate a forceps 90 comprising a pair of tines 92 and 94. From each of the tines projects a pair of highly electrically conductive tips 96 and 98 where the tips may be connected to a generator (not shown) in either a monopolar or a bipolar manner. Thus, if the tips are wired in common to the "active" output terminal, the forceps is monopolar whereas if one is wired to the "active" output terminal and the other to the "return" terminal, the forceps is bipolar. The tips are covered with an electrically insulating material 100 to prevent electrical burn. A plurality of projections are provided along the insulated portion of the tine as indicated at 102. As can be seen in the Figure the tips 96 and 98 extend relatively far into tines 92 and 94 (approximately as far as the heat radiating portion 102) to facilitate conduction of heat therefrom to the radiation area 102. Also, water cooling may be effected with this embodiment or the other embodiments by providing an appropriate thermal connection to the electrode and the water cooling system.

Figure 17:
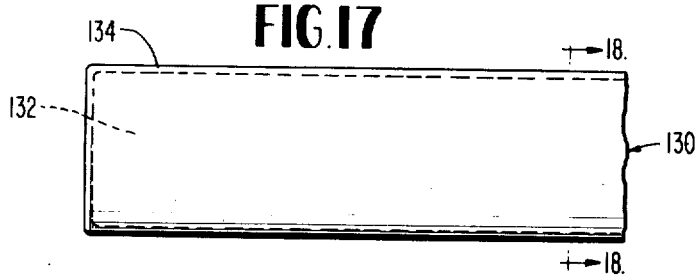
FIG. 17 is a partial side view of an illustrative blade of a monopolar electrosurgical instrument in accordance with another embodiment of the invention.
Figure 18:
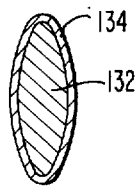
FIG. 18 is a cross-sectional view taken along the line 18—18 of FIG. 17.

Any of the electrodes discussed hereinbefore with respect to FIGS. 1 – 14 can have the heat removal and/or starting properties thereof improved whenever coated with an electrically resistive coating or the like as will be discussed in more detail hereinafter. The volume resistivity may extend from about $10^{-4}$ to $10^8$ $\Omega$-cm and preferably about 1 to $10^6$ $\Omega$-cm. A particularly suitable material is carbon. Referring to FIGS. 17 and 18, there is shown a partial side view of a blade 130 comprising a substrate 132 having a figure of merit, as discussed hereinbefore, of at least about 0.3 and a carbon containing layer 134. This blade is of the monopolar type. The carbon containing layer is preferably formed on the substrate by a pyrolytic process involving the thermal decomposition of a hydrocarbon material where a preferred hydrocarbon would be a carbohydrate. In particular, the substrate preferably has an electrosurgical cutting waveform of typically about 200 watts RF power applied thereto either prior or subsequent to the insertion of the substrate in a solid or gelatinous, carbohydrate containing substance. See U.S. Pat. No. 3,699,967 granted to Robert K. Anderson, which is hereby incorporated herein by reference, for a detailed discussion of cutting, coagulating and blended cutting waveforms typically used in electrosurgical applications. Beef or calf's liver may be employed as a carbohydrate containing substance where the activated substrate is moved through the liver. The carbohydrate in the liver is thermally decomposed and deposits on the substrate as a porous carbon coating. A blade with such a coating is typically intended for one-time use although it may be used in surgical procedures lasting 8 hours or more without substantial impairment of the carbon coating.

Another preferred method of providing a porous carbon coating for the blade is to use a thick gelatin solution which may be prepared by adding about 2 oz. of gelatin to about 1½ cups of water, heating the mixture, adding about ⅛ teaspoon salt and ⅛ cup of sugar to the heated mixture and then allowing it to cool to a gelatinous mass, it being understood that none of the foregoing amounts of ingredients are critical. Again by moving an energized substrate through the gelatin, thermal decomposition of the sugar occurs with a resulting coating of porous carbon forming on the substrate.

Because of the high thermal conductivity of the electrode materials employed in the embodiments of FIGS. 1 – 14, it is difficult but desirable to quickly raise the temperature of these electrodes to the temperature of about 100° C needed for cutting whenever the electrode is in contact with the tissue prior to electrical energization thereof. In preventing sticking and cutting in the coagulation mode it was necessary to limit electrode temperature and/or provide fast cooling. Fast cooling and fast initial heating initially appear to be steps in opposite directions. The pyrolytic carbon coating 134 helps in both situations, however. The electrical resistivity thereof provides local surface heating which decreases the electrode cutting start time by approximately a factor of 6 compared to an electrode without a coating. This provides an extremely fast start for the conventional stainless steel blade when coated and gives a coated silver blade a faster start than the uncoated stainless steel blade. The thermal resistance of the pyrolytic carbon coating increases the sticking range when heat is flowing from a hot sink to the flesh where the sticking range will be discussed in further detail hereinafter. However, it is this same thermal impedance that helps prevent sticking of the coated silver electrode when the cool sink is drawing calories from the electrode, in that it slows the heat flow to the flesh sufficiently to let it flow preferentially to the sink. A 50° C heat sunk silver blade without a carbon coating shows a greater tendency to form thin contaminating layers on itself.

In order to better understand the role of the thermal properties of the electrode, the heat sinking and carbon coatings and the like on electrosurgical electrodes, the following points should be appreciated although it is to be understood that there is no intent to be limited to a particular theory of operation:

1. It has been known that a relatively cool electrode (surface temperatures 0° – about 110° C) can provide electrosurgical desiccation without sticking to the flesh. However, it has been observed that no sparking can be involved in this process without the sticking probability becoming very great.

2. Even with a cutting waveform, a cool electrode (0° – 99° C) can not be made to cut flesh, although certain rather extreme electrical drive conditions appear to be an exception. The cool blade cannot cut because steam condenses against the metal and the establishment of a stable steam layer is prevented. The steam layer is needed to keep the metal electrode from making ohmic contact with the flesh. Ohmic contact tends to be of such low resistance that the voltages needed for sparking cannot be generated. Sparking is needed for conventional electrosurgical cutting.

3. Hot electrode cutting, in terms of using a resistance wire with current flowing through it, has been used for many years. If a coagulation electrode becomes adequately heated, it will cut by that same thermal mechanism. Thus, to avoid cutting in the coagulation mode it is necessary to restrict the electrode temperature. The electrode temperature and electrosurgical coagulation interact such that higher energy is required to cut with a cooler electrode.

Restricting electrode temperature in the coagulation mode may be done through use of large electrode heat capacities, very high crest factor waveforms, or by cooling the electrode structure in accordance with the present invention. Large heat capacity buys operating time before the electrode becomes heated sufficiently to cut. Electrode heating is roughly inverse to crest factor. It should be noted that the crest factor referred to here is that present when the electrode interacts with the flesh, not that quoted as a specification. A specification quote is determined using a resistive load where the crest factor of a periodic function is specified as the ratio of its crest (peak) value to its root-mean-square value. When sparking to meat, very considerable voltage is required before any current can flow. When voltage is present without current flow there can be no contribution toward the r.m.s. current. Thus, the effective crest factor is greater than that measured into a resistor.

Cooling of a sufficiently thermally conductive electrode in accordance with an important aspect of this invention can keep the surface temperature below the critical value, and thus avoid cutting in the coagulation mode. It should be noted that electrode geometry presents certain limitations, in that it will not be possible to remove adequate calories through electrodes that are too small in cross section, or too long. Needle electrodes thus present difficulties in this regard which are not insurmountable especially when needle electrodes of the materials and dimensions discussed hereinbefore are used.

4. In the cutting mode, electrode temperatures may rise beyond the aforementioned critical value for the coagulation mode and cause no problem. Very high blade temperatures, however, or at least unevenly heated very hot blades cut with a rough feel that is probably caused by gas buffeting. A cooled, high conductivity blade thus tends to cut very smoothly compared with a stainless steel blade of the same geometry.

5. In accordance with this invention, a unique combination of properties for an electrosurgical blade are utilized such that surface temperatures well above 110° C are employed and yet there is practically no possibility of sticking to the flesh, or fouling.

6. This combination of properties requires that the blade be formed from a material with very high thermal conductivity (TC preferably greater than about 0.3 metric). This makes silver (1.0), copper (1.0), gold (0.7), carbon (0.5), beryllia (0.5), tungsten (0.5), and molybdenum (0.4) and some possible alloys of these, primary materials for electrode construction. High thermal conductivity is a necessary but not a sufficient condition for this high temperature non-sticking behavior.

7. When pressed to flesh prior to applying RF power, such a high conductivity blade is very slow to start the cutting mode, in that a surface temperature of 100° C must be established to achieve the cutting. The high conductivity bleeds the heat away from the tip making it difficult to quickly reach this temperature although it is to be understood that this temperature is quickly reached when RF power is applied prior to contacting the flesh or tissue with the blade.

8. The electrically resistive coating 134 on a highly thermally conductive electrode can provide fast starting whenever the electrode is contacted with the flesh prior to RF energization thereof. The coating 134 may also exhibit thermal resistance properties. Further, such an electrode can be compatible with non-sticking properties. Carbon, especially that applied by pyrolytic processes discussed hereinbefore, provides such a coating.

This somewhat porous carbon coating provides electrical resistance, R. The passage of large currents, I, through the carbon when the electrode is in physical contact with the flesh produce $I^2R$ heating. This increased heating brings the electrode to required temperature about six times faster than in its absence. The porosity of the carbon coating formed by RF sparking to certain conductive hydrocarbon bearing materials may provide thermal resistance which permits a surface temperature somewhat greater than the bulk temperature. This effect must be sufficiently small that the mechanism explaining the sticking of stainless steel electrodes is not significantly invoked as the electrode cools. Approximately the same speed-up factor applies regardless of electrode material. Thus a carbon coated stainless steel blade is also a fast starter. However, carbon on silver or copper gives a start that is faster than that with bare stainless steel. This type of coating is thus of value on many possible electrode materials. Even though the ohmic phase resistance is increased by the coating, the electrode heating in the sparking phase does not appear to be noticeably changed.

9. Non-sticking properties for a heat sinked high temperature electrode appear to be dependent upon volume heat capacity, in conjunction with the other properties. The mechanism for high temperature non-sticking (above about 300° C as will be illustrated in more detail hereinafter with respect to FIG. 27) appears to be that of supplying to the flesh sufficient energy in a short enough time. This then sears and seals the surface of the flesh rather than just bursting cells to produce a sticky coagulum. Ideally, the electrode then should cool fast enough that it cannot conveniently be moved to moist flesh while still above 110° C.

For each design combination of materials (heat capacity, thermal conductivity, density, and coating), geometry (length, cross section, and taper), and heat sink (heat capacity, and thermal impedance to the electrode), along with application situation (blade and sink temperatures at time of contact, electrode area exposed to fresh flesh, pressure against flesh, nature of flesh, and time of contact) there will be a range of conditions that will cause sticking or fouling. It is assumed for simplicity that the sink conditions are standardized, as is the application situation. There is then a range of blade temperatures (about 100° C to 300° C, as mentioned hereinbefore and as will be illustrated in more detail hereinafter with respect to FIG. 27) within which touchdown will transfer inadequate energy, or energy at an inadequate rate, and fouling will result. When the hot blade is held in air, and not touched down, the sink will pull the heat away, bringing the blade through this range of problem temperatures. The period of time that it takes the system to pass through this problem temperature range may be termed the "period of jeopardy."

There is thus a period of jeopardy in both the heating and cooling of the electrode in which stopping the electrosurgical current and touching fresh flesh could result in possible fouling. This critical period is made very short in duration in accordance with this invention.

Consider a stainless steel electrode. It has very poor thermal conductivity (about 20 times less than silver). It does have rather high volume heat capacity, however, Because the heat generated at the tip cannot be adequately conducted up the electrode to a sink, the tip becomes very hot — often close to red heat. This very high and uneven temperature contributes a turbulence to the steam flowing from the sparking region. This buffets the blade, giving a very rough feel to the cutting action. When cutting current is stopped, and the electrode is touched to fresh flesh (not containing a substantial amount of carbohydrates such as the beef liver referred to hereinbefore). The high temperature starts to sear the flesh. However, due to the very poor thermal conductivity, the blade surface cools almost immediately upon contact. Sufficient energy cannot be transferred fast enough to seal the flesh without forming a sticky coagulum. With this material on the blade surface, the heat continues to flow, drying the adherent to a hard, non-conducting coating. The period of jeopardy for a 1 inch long stainless steel electrode formed from 0.051 inch diameter stock (the electrode has an elliptical cross section of area the same as a 0.051 inch diameter circle) is up to about 5 seconds, depending upon the initial temperature. Jeopardy reaches to very high temperatures for stainless. For a heated silver electrode the initial energy transfer is sufficient to sear the tissue to a dry surface that will not stick. The period of jeopardy for a 1 inch silver blade is typically about 0.3 seconds. At ⅜ inch length, the period appears to be the order of 0.1 second. Considerable skill is required to move the electrode to fresh flesh and touchdown during the critical period. If you move too fast, the new site sears dry, if too slowly, no reaction occurs or only slight blanching. It is only during the very short period of jeopardy that touching flesh will cause fouling. About 260° C is the upper bound of jeopardy for a short silver electrode. Tip temperature cannot become excessive due to the thermal condition to the sink, thus a very smooth cutting action is effected with a silver electrode.

10. This period of jeopardy on the falling temperature characteristic is quite independent of the electrosurgical generator. The same is not true of the period occurring in the rising temperature characteristic. The time in operation required to get safely through the critical electrode temperature zone depends on all of the factors that have been mentioned, and in addition, the output level of the generator. The problem now is not a touching of fresh flesh with a partially heated electrode, as much as it is getting the flesh under the initial touchdown dry enough before the period of jeopardy arrives on the way up. A high thermal conductivity electrode at low power could be very slow in its temperature rise. The use of the resistive coating (carbon, for example) again is helpful, concentrating the heat at the blade surface, and more rapidly heating the electrode in the ohmic contact phase.

Figure 27:
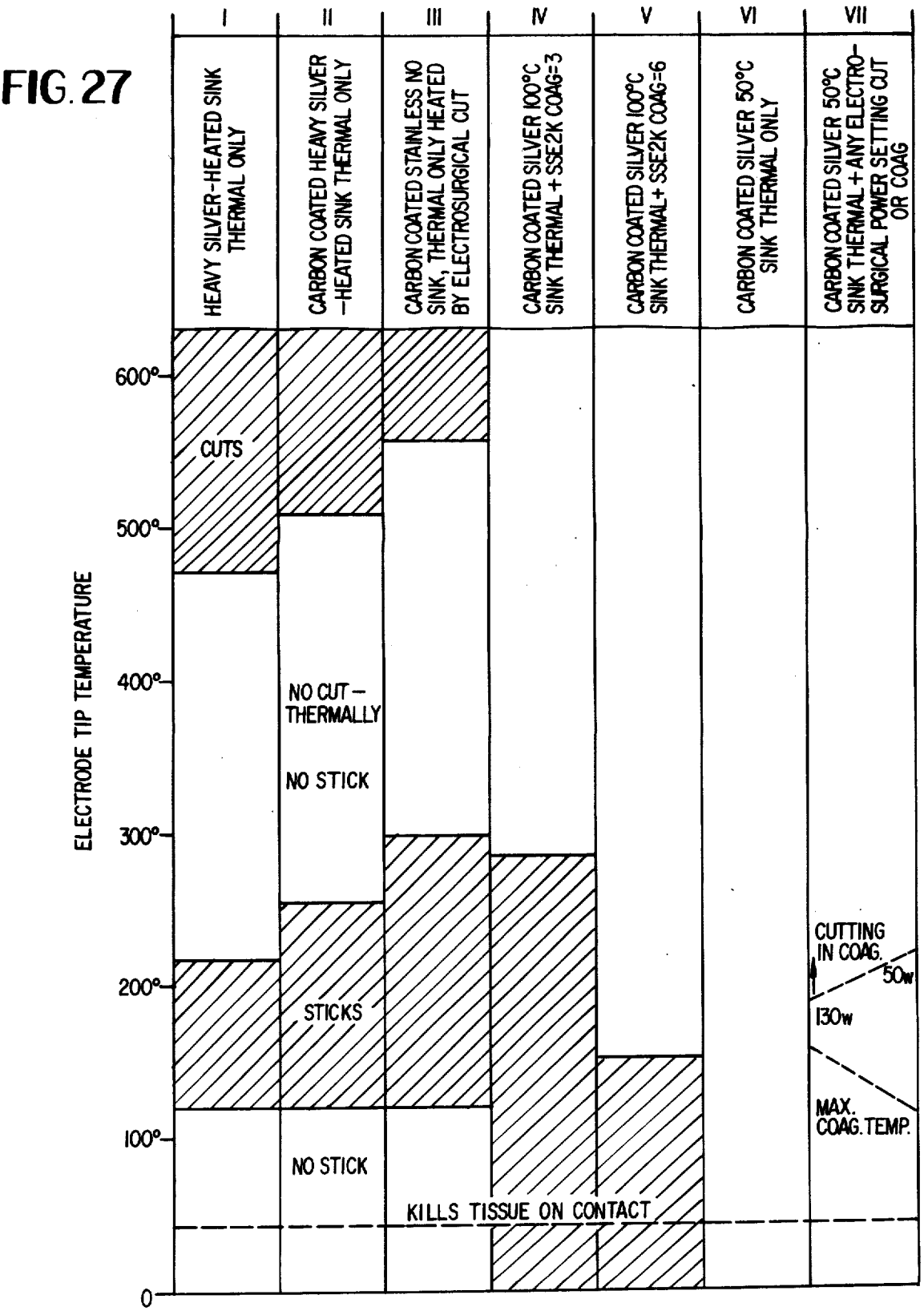
FIG. 27 is a chart illustrating the results of various experiments conducted to demonstrate factors involved in the non-sticking feature of the electrodes of this invention.

In order to further illustrate how the present invention substantially eliminates electrode fouling, the following experiments were conducted, the results of which are illustrated in FIG. 27. A massive heat sink was attached to certain ones of electrodes such that approximately ⅜ inch of electrode extended out of the sink where the sink comprised a block of aluminum or copper about ½ inch square and 3 inch long. Pyrolytic carbon coatings were placed on certain ones of the blades in accordance with the carbohydrate thermal decomposition techniques mentioned hereinbefore. The electrodes had elliptical cross sections area the same as a 0.051 inch diameter circle. The sink was heated by an acetylene torch or the like in certain tests and then time for thermal equilibrium was allowed to occur. The electrode was then touched to fresh beef liver. The behavior of the electrode was then observed where the electrode and sink temperatures were measured by attached thermocouples.

The electrode of Column III was stainless steel with a thin carbon coating. The electrode was heated by applying an electrosurgical cutting waveform thereto and then the liver was cut to raise the temperature of the blade. The blade was then removed and the cutting waveform removed therefrom. When it decreased to a desired temperature it was touched to fresh flesh. This procedure was repeated over the temperature range of interest. The electrode did not stick to the flesh until its temperature at time of touchdown was approximately 120° C, even though physiological tissue damage started at about 46° C. This was true of all electrodes tested. The stainless electrode stuck to the flesh when its touchdown temperature was between 120° C and 305° C. At initial temperatures greater than 305° C this electrode desiccated and necrosed the tissue it touched, but it did not stick to it. Initial energy transfer was sufficient to give a dry coagulum. When the electrode temperature exceeded about 580° C, the electrode cut the flesh easily by thermal means alone, all of the foregoing being illustrated in Column III. Stainless steel has very low thermal conductivity and rather high volume specific heat.

This experiment was repeated as illustrated in Column II substituting a carbon coated silver electrode of the same dimensions. Also the blade was heated by heating the sink as described above rather than by the electrosurgical cutting method described in Column III. The cutting temperature was lowered to 510° C, and the sticking range was 120° C to 260° C. This direction of change was not unexpected, in that silver is about 10–20 times a better thermal conductor than the stainless steel. Both sticking and cutting require calories from the electrode. The better the thermal conductivity, the easier it is to transfer calories from the heat sink to the flesh. Removing the carbon layer from the silver electrode lowered both cutting and sticking temperatures by 40° C as illustrated in Column I. Thus at least one role of the carbon coating would appear to be that of a heat flow barrier, although it should be understood that the thermal resistance of the coating on the electrode must not be so great as to introduce fouling thereof due to the slowdown in removing heat from the electrode.

The heat sink of the carbon coated silver electrode of Column II was then forced to be less than 150° F (66° C) such as the 50° C shown in Column VI. The sink temperature can be readily lowered by bringing it into contact with a cold material such as ice or the like. The electrode was independently heated by applying an electrosurgical cutting waveform thereto as described hereinbefore with respect to Column III. When the electrode was well above the temperatures of interest, it was removed from the incision, the electrosurgical generator was stopped, and the flesh was touched with the electrode tip as it crossed the temperatures of note. Under these conditions this electrode did not stick regardless of its temperature. Because of the cool sink and high blade thermal conductivity, the blade temperature dropped very rapidly. The preferred path of heat transfer was to the sink. Insufficient energy was transferred to the meat to cause the sticking reaction when the blade temperature was about 260° C or below, and at higher temperatures the heat transfer to the meat was sufficient to form a dry coagulum which did not stick. The electrode temperature fell through any critical zone (period of jeopardy)before the electrode could be moved to a fresh location.

Thus far, the experiments were directed to electrodes that were heated or cooled, but not electrosurgically enpowered. That is, thus far, the blades were heated by heating the sink or by an electrosurgical cut and then applied to the tissue without an electrosurgical waveform being applied thereto. Now when the heated blade is applied to the tissue, an electrosurgical waveform will also be applied to the blade. The results of these tests are shown in Columsn IV, V and VII. The interaction of thermal and electrosurgical effects was thus next tested. With stainless electrodes, a very short burst of power can bring local electrode temperatures into the sticking range. Because of the high thermal conductivity, silver and copper electrodes tend to be very free of this short burst sticking. It should be appreciated that unusual force between any electrode and the flesh can cause the electrode to break through a dry coagulum layer. If the electrode is in the sticking temperature range at the time of break-through, a fouled electrode will typically result. This effect is rather independent of electrode thermal properties. However, this period of jeopardy is very short in duration for the high conductivity electrodes of this invention.

In the experiments illustrated in Columns IV and V, the heat sink was near 120° C (100° C) when a short burst of electrosurgical coagulation power was applied. The resultant electrode temperature was quickly pushed into the sticking range. Because of the low temperature differential to the sink the electrode was held in the sticking temperature range for a significant time period. The higher the power setting, the easier the electrode reached a surface temperature state and electrosurgical interaction that provided dry coagulum against which the hot electrode could safely rest. This behavior is shown in Columns IV and V of FIG. 27, wherein Columns IV and V, coagulation waveforms were applied to the electrode from an SSE 2K Electrosurgical Generator made by Valleylab, Inc. of Boulder, Colorado, where the setting of coag = 3 corresponds to a power level of approximately 25 watts and the setting of coag = 6 corresponds to about twice as much power. It is obviously undesirable for the heat sink to approach the high temperatures of Columns IV and V.

If the sink is cooled to 50° C (as in Column VI and VII) or below, it is found that the blade temperature and electrosurgical interaction do not force the sticking situation to be easily generated. Again the electrode seemed to spend so little time in any critical temperature zone that no consistent sticking was located. At temperatures between 260° C and 120° C where sticking was expected, none was observed. It appears that the formation of a sticky coagulum requires both initial temperature and then a longer period at that same or a lesser temperature above about 100° C. The high conductivity system with a cool heat sink can have the initial electrode temperature requirements for sticking, but then the electrode cools very quickly to near sink temperature. The result is failure to stick to the flesh. In the cutting mode (as in Column VII) the blade tip temperature can build to about 450° C with extended heavy use, in spite of the sinking. However, once the cutting ceases, the behavior is that of Column VI — no sticking. In the coagulation mode (as also in Column VII) the heating is very slight. The heat sunk silver blade seldom attains temperatures significantly above 120° C. When coagulation ceases, the behavior is again that of Column VI — no sticking.

The interaction of electrosurgical power with the high conductivity electrode with heat sinking provides no detected periods of jeopardy. Such periods probably exist, depending upon many factors, but they are so short that detecting them experimentally has proved to be frustrating.

Massive cutting in the coagulation mode depends in part on coagulation power level, and much upon crest factor (CF), but these interact heavily with electrode temperatures. For example, if CF = 6 power at 50 watts, cutting occurs at about 220° C electrode tip temperature as shown in Column VII. Increasing to 130 watts moves the starting of cutting down to about 190° C as can also be seen in Column VII. Conventional stainless steel electrodes achieve the cutting temperature with about 70 watts under these conditions. Even at 130 watts a correctly heat sinked high thermal conductivity electrode however does not achieve 190° C, and will not cut in the coagulation mode as again illustrated in Column VII. Electrode material and sink properties can thus compensate for crest factor limitations in preventing massive cutting in the coagulation mode. Effective crest factor is doubly important in that with greater crest factor, the depth and effectiveness of the coagulation is improved. Also with greater crest factor, the electrode temperature at which cutting can occur is increased and electrode heating is decreased.

In addition to the pyrolytic coating embodiment discussed hereinbefore with respect to the embodiment of FIGS. 17 and 18, other embodiments corresponding to these figures may also be employed where the heat sinking described in the embodiments of FIGS. 1 - 14 may or may not be used. Thus, substrate 132 may be made from metallic material such as copper, silver, or stainless steel or a hard, high temperature material, such as beryllia, which could be metallized. The substrate 132 may be coated with an electrically resistive coating 134 consisting essentially of carbon or the like.

The carbon may be suspended or dispersed in an appropriate binder and coated on the substrate. The binder may be an epoxy binder such as that sold under the name "Five-Minute Epoxy" by Devcon Co. or any other suitable plastic binder. The carbon may comprise ground up amorphous graphite dispersed in any of the above binders or that sold under the name "Graphibond" by Aremco Co.

Alternatively the carbon or other material may be sputter or vapor deposited as a thin film on substrate 132. Thus, stainless steel electrodes coated with approximately 8000 angstroms of carbon have been investigated, it being understood that the invention is not limited to this thickness. The thickness should preferably be between 6000 angstroms and 10,000 angstroms for coatings applied in this manner. Thicker (up to several mils), better bonded coatings are obtained by the pyrolytic coating method described hereinbefore where radio frequency sparking occurs in certain carbohydrate containing materials. It has been determined that such thin film electrodes lend themselves to disposability. The required low production costs for disposable electrodes necessitates mass production with simple, preferably automated manufacturing steps. Vacuum deposition and pyrolytic formation of coatings falls within this category of steps. Deposition of adherent carbon coatings on metals such as stainless steel can be effected as follows. The stainless steel parts are "sputter cleaned" in vacuum, or alternately chemically cleaned. A thin coating of approximately 500 angstroms of titanium is "sputtered" onto the stainless steel to serve as a bonding layer. Then carbon is sputtered onto the titanium, and the process continued until the required carbon thickness is attained. Also electron beam evaporating may be used to deposit carbon or the like on a titanium coated stainless steel or other metallic substrate.

If the substrate 132 is electrically conductive, it would be connected to the active output terminal of an electrosurgical generator (not shown) in a manner well known in this art. If the substrate 132 is non-conductive, the carbon coating would be connected to the active output terminal of the generator by means of conductive fingers (not shown) or the like. The indifferent electrode (not shown), as is well known, would comprise a relatively large surface area pad connected to a nonsurgical site and connected to the return terminal of the generator.

Figure 15:
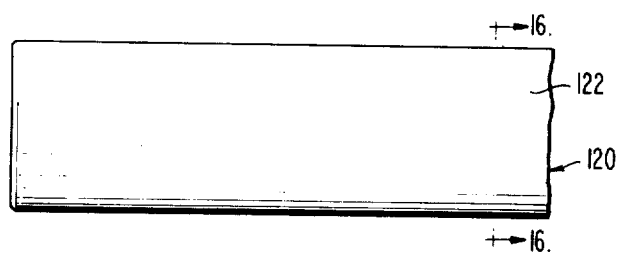
FIG. 15 is a partial side view of an illustrative carbon coated blade of a monopolar electrosurgical instrument in accordance with another aspect of the invention.
Figure 16:
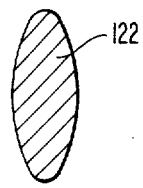
FIG. 16 is a cross-sectional view taken along line 16—16 of FIG. 15.

Referring now to FIGS. 15 and 16, another embodiment of a monopolar instrument 120 will be described. The blade of this instrument comprises a monolithic, electrode shaft 122 made of the materials from which layer 134 of FIG. 17 may be made. Preferably these materials would be in substantially crystalline form such as graphite with appropriate filler material, if desired. Further, the heat sinking described hereinbefore with respect to the embodiments of FIGS. 1 - 14 may or may not be used. In this embodiment the blade is connected by appropriate electrical contacting means to the active electrode of the generator and the indifferent electrode connection is as described above in connection with the embodiment of FIGS. 17 and 18. There are desirable properties which may be associated with monolithic carbon or carbon coated electrodes. These properties, such as simultaneous coagulation, decreased sticking or fouling, decreased stimulation currents, faster starting and reduced operating power, are as described in detail hereinbefore.

A possible explanation in the self cleaning nature of the carbon/graphite coated blades and monolithic blades during a cutting procedure is the surface oxidation of the electrodes. The carbon oxides are, of course, gases, thus, they do not remain on the surface or provide insulation build-up. Instantaneous surface temperatures at arc spark sites are probably at least the 400 C needed for oxidation of the carbon in air. The microscopic pits formed by this oxidation leave ridges which become the preferred sites for subsequent spark generation. This mechanism thus promotes surface uniformity as the oxidation removes surface material. This oxidation is fast enough to keep the surface clean, but is sufficiently slow that the electrode is usable for extended operations without noticeable "wear" or material loss.

Figure 19:
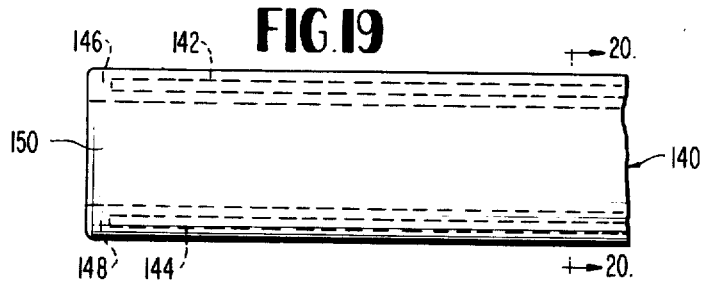
FIG. 19 is a partial side view of an illustrative blade of a bipolar electrosurgical instrument in accordance with another embodiment of the invention.
Figure 20:
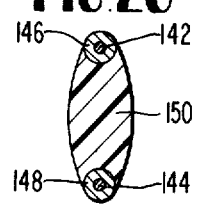
FIG. 20 is a cross-sectional view taken along the line 20—20 of FIG. 19.

Referring to FIGS. 19 and 20, there is shown a blade 140 of a bipolar electrosurgical instrument comprising substrate shafts 142 and 144, electrode coating layers 146 and 148 respectively coated upon substrate shafts 142 and 144 and insulative body 150 for supporting coated, substrate shafts 142 and 144. The substrate shafts 142 and 144 may be made of the same materials as substrate 132 of FIG. 17 while coverings 146 and 148 may comprise the same materials as those comprising layers 134 of FIG. 17. Insulative body 140 may comprise ceramic, glass or the like.

The bipolar instrument may be connected to an electrosurgical generator where, if shafts 142 and 144 are made from an electrically conductive material, these shafts are respectively connected to the output terminals of the generator and if they are made of a non-conductive material the output terminals of the generator are respectively directly connected to the coating layers 146 and 148.

Figure 21:
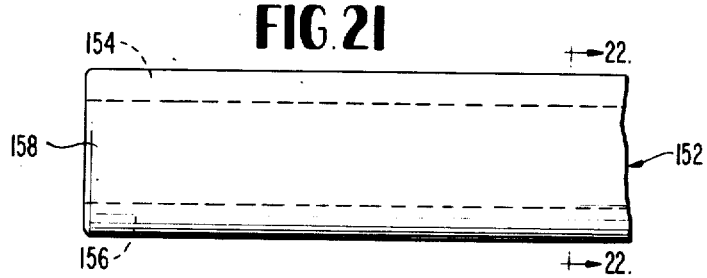
FIG. 21 is a partial side view of an illustrative blade of a bipolar electrosurgical instrument in accordance with another embodiment of the invention.
Figure 22:
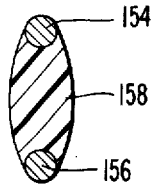
FIG. 22 is a cross-sectional view taken along the line 22—22 of FIG. 21.

Referring to the embodiment of FIGS. 21 and 22, there is shown another bipolar instrument, which is analogous to the monopolar instrument of FIGS. 15 and 16. Thus, the blade 152 comprises an electrode 154 and an electrode 156 where each of the electrodes is made from material similar to that of the electrode of FIGS. 15 and 16. The electrodes are separated by an insulative support body 158. The electrodes 154 and 156 are respectively connected to the output terminals of the generator.

Figure 23:
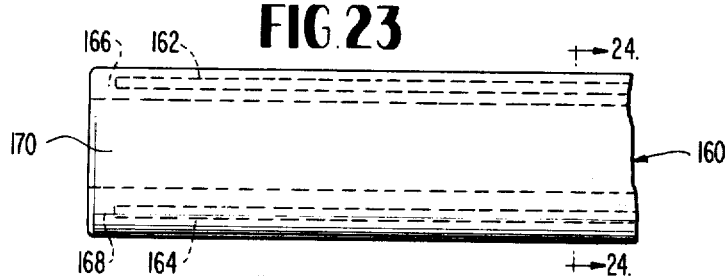
FIG. 23 is a partial side view of an illustrative blade of a sesquipolar electrosurgical instrument in accordance with another embodiment of the invention.
Figure 24:
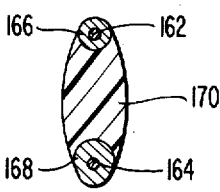
FIG. 24 is a cross-sectional view taken along line 24—24 of FIG. 23.

Referring to FIGS. 23 and 24, there is shown a sesquipolar instrument which is analogous to the monopolar instrument of FIG. 17 and the bipolar instrument of FIG. 19. Thus blade 160 comprises substrate shafts 162 and 164, electrode covering layers 166 and 168 respectively coated on substrate shafts 162 and 164 and insulative body 170 for supporting covered substrate shafts 162 and 164. The materials comprising substrate shafts 162 and 164, coating layers 166 and 168 and insulative body 170 respectively correspond to those disclosed for substrate shafts 142 and 144, electrode coating layers 146 and 148, and insulative body 150 of blade 140. Further, the electrical connections to the blade of FIG. 23 correspond to those described hereinbefore for the blade of FIG. 19.

Figure 25:
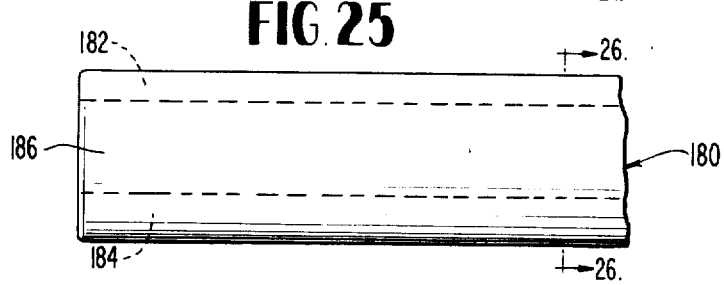
FIG. 25 is a partial side view of a blade of another sesquipolar electrosurgical instrument in accordance with another embodiment of the invention.
Figure 26:
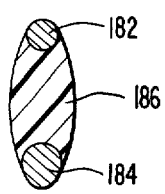
FIG. 26 is a cross-sectional view taken along the line 26—26 of FIG. 25.

Referring to FIGS. 25 and 26, there is described another sesquipolar electrosurgical instrument, which is analogous to the bipolar instrument of FIG. 21. Thus, the materials comprising electrodes 182 and 184 and insulative body 186 of blade 180 respectively correspond to those described for electrodes 154 and 156 and insulative body 158 of the FIG. 21 embodiment. Further, the electrical connections to the FIG. 25 blade are the same as those for the FIG. 21 blade.

It should be appreciated that, although generally illustrated for electrosurgical knives, carbon may be employed in accordance with the invention in electrodes of other surgical devices such as forceps, needles, etc.

The electrodes of this invention with both a single cutting edge and a coagulation surface may make practical a very simple electrosurgical generator with only a "Cut" waveform which could be used for the entire electrosurgical function. Reference should be made to the beforementioned co-pending application for electrode configurations in which both a cutting surface and a coagulation surface may be incorporated. In particular, note the embodiment of FIGS. 38 - 41. It should be further noted that the electrodes of the present invention can be incorporated into all of the structures shown in the beforementioned, co-pending application. Further, the thin film, carbon coatings are thin enough and sufficiently adherent that the blade can be bent quite sharply (90° with ⅛ inch radius) and straightened without loosening the coat. This property is important and unique. It has also been observed with electrodes comprising carbon coated substrates that heating preferentially occurs in the carbon coating. This coating has a higher resistivity and/or power density when compared with the other components present in the series path followed by the electric current such as the electrode substrate, the patient's body, and the indifferent electrode. Hence, surgical procedures are initiated faster and with less power. Less power, in turn, results in less current through the patient, less tissue damage, cooler electrode operation and potential simplification of the electrosurgical generator.

Figure 28:
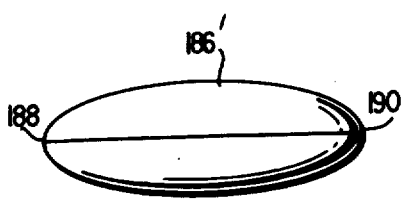
FIGS. 28, 29 and 30 are end, side and front views respectively of illustrative blades in accordance with this invention where the cross section thereof is elliptical in configuration.
Figure 29:
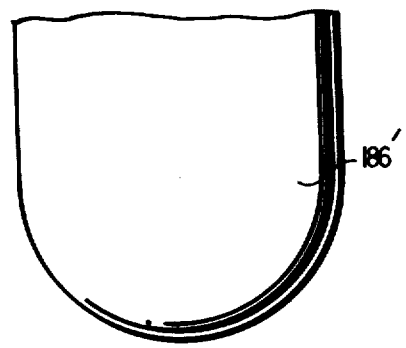
Figure 30:
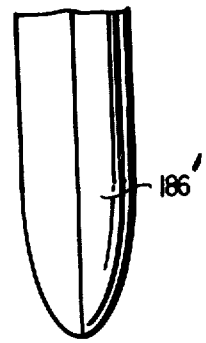

Referring to FIGS. 28, 29 and 30, the blades described hereinbefore may have a cross section through a first plane, as illustrated in FIG. 28, perpendicular to the longitudinal axis of the blade 186 where the cross section is of an elliptical configuration. Such elliptical configurations are known. Extreme sharpness at the forward and rearward edges 188 and 190 are thus avoided thereby enabling the blade to cut tissue only when empowered with RF electrosurgical "cutting" waveforms. However, due to the thermal properties of the blades discussed hereinbefore, it is, in some instances, desirable to give them a sharper "cutting" edge than is customary with stainless steel blades and the like. The embodiments illustrated in FIGS. 31 through 33 and 34 through 36 do effect the foregoing while at the same time, leaving the cross sectional area thereof substantially unchanged whereby the heat flow properties thereof remain unaffected.

Figure 31:
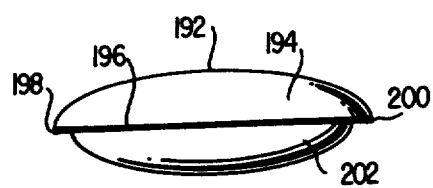
FIGS. 31, 32 and 33 are end, side and front views respectively of further illustrative blades in accordance with this invention where each longitudinal half of the blade has a cross section of semi-elliptical configuration where the major radii of the elliptical configuration of one half is different from that of the other.
Figure 32:
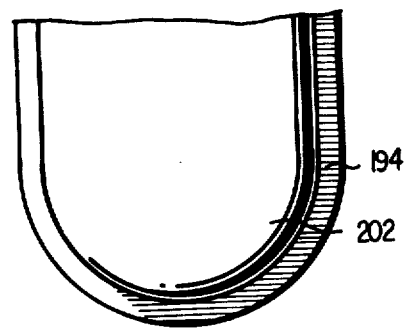
Figure 33:
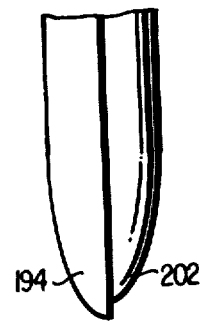

Thus, in the embodiment of FIGS. 31 through 33, the cross section through a first plane (illustrated in FIG. 31) perpendicular to the longitudinal axis of the blade 192 has a first semi-elliptical configuration 194 on one side of a second plane indicated at 196 extending along the longitudinal axis of the blade from the forward end 198 to the rearward end 200 thereof. A second semi-elliptical configuration on the opposite side of the second plane is illustrated at 202, the two major radii of the second semi-elliptical configuration 202 being less than those of the configuration 194.

Figure 34:
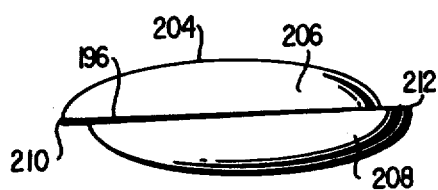
FIGS. 34, 35 and 36 are end, side and front views respectively of a further illustrative blade in accordance with this invention where each longitudinal half of the blade has a semi-elliptical cross section where each half is offset with respect to the other half.
Figure 35:
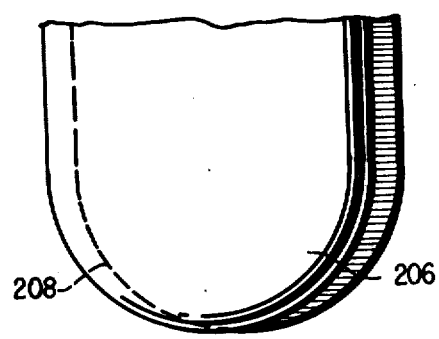
Figure 36:
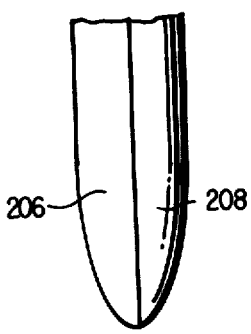

Referring now to the embodiment of FIGS. 34 through 36, the cross section through the first plane, indicated in FIG. 34, perpendicular to the longitudinal axis of the blade 204 has a first semi-elliptical configuration 206 on one side of the second plane 196 and a second semi-elliptical configuration 208 on the opposite side thereof where the first and second configurations 206 and 208 are substantially equal in size and offset with respect to one another along plane 196. Thus, note edges 198 and 200 of FIG. 31 and 210 and 212 of FIG. 34 are substantially sharper than the edges 188 and 190 of FIG. 28. Hence, the sharper edges of the FIGS. 31 and 34 embodiments tend to offset the high thermal conductivity characteristics of the blade to thereby facilitate the establishment and maintenance of effective cutting conditions.

What is claimed is:

1. An electrosurgical instrument comprising
    a support member;
    at least one electrode mounted on said support member, said electrode comprising (a) a substrate consisting essentially of a material having a figure of merit of at least 0.15 at room temperature where said figure of merit is the product of the thermal conductivity, the heat capacity and the density of said material in the metric system, and (b) an electrically resistive coating disposed on said substrate, the volume resistivity of said coating extending from about $10^{-4}$ to $10^8 \Omega$-cm.
    ridged heat radiating means in thermal contact with said electrode for radiating heat into the medium surrounding said electrode, said heat radiating means being covered by a ridged electrically insulative cover and
    means for connecting said electrode to a source of electrosurgical energy.

2. An instrument as in claim 1 where said figure of merit is at least 0.3.

3. An instrument as in claim 1 where said electrode material is selected from the group consisting of copper, silver, gold, metallized beryllia, carbon, tungsten, and molybdenum.

4. An instrument as in claim 1 where said electrode is removably mounted on said support member.

5. An instrument as in claim 1 comprising a forceps, said support member comprising the forceps tines which have respective distal ends and a pair of said electrodes being respectively mounted at the distal ends of said tines each of said electrodes including a radiating means covered by an insulative cover and a means for connecting to source to a source of electrosurgical energy.

6. An electrode for an electrosurgical instrument comprising (a) a substrate consisting essentially of a material having a figure of merit of at least 0.15 at room temperature where said figure of merit is the product of the thermal conductivity, the heat capacity and the density of said material in the metric system, and (b) an electrically resistive coating disposed on said substrate, the volume resistivity of said coating extending from about $10^{-4}$ to $10^8 \Omega$-cm;
means for connecting said substrate to a source of electrosurgical energy, and means for attaching said substrate to an electrosurgical instrument.

7. An electrode as in claim 6 where said figure of merit is at least 0.3.

8. An electrode as in claim 6 where said electrode material is selected from the group consisting of copper, silver, gold, metallized beryllia, carbon, tungsten, and molybdenum.

9. An electrode as in claim 6 comprising a blade.

10. An electrode as in claim 6 comprising a needle.

11. An electrode as in claim 6 where said volume resistivity range is about $1 - 10^6 \Omega$ -cm.

12. An electrode as in claim 6 where said electrically resistive coating consists essentially of carbon.

13. An electrode as in claim 12 where said coating is porous.

14. An electrode as in claim 13 where said coating is formed on said substrate by thermal decomposition of a carbohydrate containing material.

15. An electrode as in claim 14 where said coating is formed by heating said substrate and moving it through said carbohydrate containing material.

16. An electrode as in claim 13 where said coating layer includes said carbon and a binder therefor.

17. An electrode as in claim 13 where said coating layer comprises a vapor deposited thin film of said carbon.

18. An electrode as in claim 13 where said coating layer comprises a sputtered thin film of said carbon.

19. An electrosurgical instrument comprising
a support member;
at least one electrode mounted on support member, said electrode comprising (a) a substrate consisting essentially of a material having a figure of merit of at least 0.15 at room temperature where said figure of merit is the product of the thermal conductivity, the heat capacity and the density of said material in the metric system, and (b) an electrically resistive coating disposed on said substrate, the volume resistivity of said coating extending from about $10^{-4}$ to $10^8 \Omega$-cm; and
means for connecting said electrode to a source of electrosurgical energy.

20. An instrument as in claim 19 where said figure of merit is at least 0.3.

21. An instrument as in claim 19 where said electrode material is selected from the group consisting of copper, silver, gold, metallized beryllia, carbon, tungsten, and molybdenum.

22. An instrument as in claim 19 where said electrode is removably mounted on said support member.

23. An instrument as in claim 19 comprising a forceps, said support member comprising the forceps tines which have respective distal ends and a pair of said electrodes being respectively mounted at the distal ends of said tines, each of said electrodes including a means for connecting to a source of electrosurgical energy.

24. An instrument as in claim 19 where said electrically resistive coating consists essentially of carbon.

25. An instrument as in claim 24 where said coating is porous.

26. An instrument as in claim 25 where said coating is formed on said substrate by thermal decomposition of a carbohydrate containing material.

27. An instrument as in claim 26 where said coating is formed by heating said substrate and moving it through said carbohydrate containing material.

28. An instrument as in claim 24 where said coating layer includes said carbon and a binder therefor.

29. An instrument as in claim 24 where said coating layer comprises a vapor deposited thin film of said carbon.

30. An instrument as in claim 24 where said coating layer comprises a sputtered thin film of said carbon.

31. An instrument as in claim 19 where said electrode comprises a blade mounted on said support member.

32. An instrument as in claim 31 where the cross section through a plane perpendicular to the longitudinal axis of said blade has an elliptical configuration.

33. An instrument as in claim 19 including two of said electrodes of the same size mounted on said support member where both electrodes consist essentially of said material having said figure of merit, each of said electrodes including a means for connecting to a source of electrosurgical energy.

34. An instrument as in claim 33 where each of said electrodes comprises a needle.

35. An instrument as in claim 19 including two of said electrodes of different size mounted on said support member, each of said electrodes including a means for connecting to a source of electrosurgical energy.

36. An instrument as in claim 35 where the larger size electrode of said two different size electrodes consists essentially of said material having said figure of merit.

37. An electrosurgical instrument comprising
a support member;
at least one electrode mounted on said support member where said electrode includes an electrically resistive coating disposed on a stainless steel substrate, the volume resistivity of said coating extending from about $10^{31\ 4}$ to $10^8 \Omega$-cm and
means for connecting said electrode to a source of electrosurgical energy.

38. An instrument as in claim 37 where said volume resistivity range is about $1 - 10^6 \Omega$-cm.

39. An instrument as in claim 37 where said electrically resistive coating consists essentially of carbon.

40. An instrument as in claim 39 where said coating is porous.

41. An instrument as in claim 40 where said coating is formed on said substrate by thermal decomposition of a carbohydrate containing material.

42. An instrument as in claim 41 where said coating is formed by heating said substrate and moving it through said carbohydrate containing material.

43. An instrument as in claim 40 where said coating layer includes said carbon and a binder therefor.

44. An instrument as in claim 40 where said coating layer comprises a vapor deposited thin film of said carbon.

45. An instrument as in claim 40 where said coating layer comprises a sputtered thin film of said carbon.

46. An electrosurgical instrument comprising
a support member;
at least one blade mounted on said support member, said blade having forward and rearward ends and comprising a material having a figure of merit of at least 0.15 at room temperature where said figure of merit is the product of the thermal conductivity, the heat capacity and the density of said material in the metric system where the cross section through a first plane perpendicular to the longitudinal axis of said blade has a first semi-elliptical configuration on one side of a second plane extending along said longitudinal axis of the blade from the forward to rearward ends thereof and a second semi-elliptical configuration on the opposite side of said second plane where the two major radii of said second semi-elliptical configuration are less than those of said first semi-elliptical configuration; and
means for connecting said blade to a source of electrosurgical energy.

47. An electrosurgical instrument comprising
a support member;
at least one blade mounted on said support member, said blade having forward and rearward ends and comprising a material having a figure of merit of at least 0.15 at room temperature where said figure of merit is the product of the thermal conductivity, the heat capacity and the density of said material in the metric system where the cross section through a first plane perpendicular to the longitudinal axis of said blade has a first semi-elliptical configuration on one side of a second plane extending along said longitudinal axis of the blade from the forward to rearward ends thereof and a second semi-elliptical configuration on the opposite side of said second plane where said first and second semi-elliptical configurations are substantially equal in size and are offset with respect to one another along said second plane; and
means for connecting said blade to a source of electrosurgical energy.

* * * * *